(12) United States Patent
Gebhardt et al.

(10) Patent No.: US 6,261,581 B1
(45) Date of Patent: Jul. 17, 2001

(54) USE OF POLYMERS AS BIOCIDES

(75) Inventors: Norbert Gebhardt, Neustadt; Dieter Zeller, Wiesloch; Claudia Nilz, Rödersheim-Gronau; Ulrich Steuerle, Heidelberg, all of (DE); Charlotte Johansen, Holte (DK)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/142,219

(22) PCT Filed: Mar. 4, 1997

(86) PCT No.: PCT/EP97/01082

§ 371 Date: Sep. 3, 1998

§ 102(e) Date: Sep. 3, 1998

(87) PCT Pub. No.: WO97/32477

PCT Pub. Date: Sep. 12, 1997

(30) Foreign Application Priority Data

Mar. 6, 1996 (DE) ................................ 196 08 555

(51) Int. Cl.$^7$ .................................................. A01N 33/04
(52) U.S. Cl. .................... 424/405; 424/78.08; 424/78.35
(58) Field of Search ..................................... 424/405, 409, 424/78.08, 78.31, 78.32, 78.35

(56) References Cited

U.S. PATENT DOCUMENTS

| | | | |
|---|---|---|---|
| 3,714,259 | 1/1973 | Lichtenwalter | 260/583 |
| 4,444,667 | 4/1984 | Burkert et al. | 210/735 |
| 4,463,193 | 7/1984 | Johnson et al. | 564/479 |
| 4,880,497 | 11/1989 | Pfohl et al. | 162/135 |
| 5,300,287 * | 4/1994 | Park | 424/78.04 |
| 5,578,598 * | 11/1996 | Abe et al. | 514/255 |
| 5,658,915 * | 8/1997 | Abe et al. | 514/255 |
| 5,739,190 * | 4/1998 | Hartmann et al. | 524/310 |
| 6,162,391 * | 12/2000 | Kowata et al. | 422/16 |

FOREIGN PATENT DOCUMENTS

| | | |
|---|---|---|
| 331528 | 9/1989 | (EP) . |
| 1071630 | 6/1982 | (SU) . |
| 97/32480 * | 9/1997 | (WO) . |

OTHER PUBLICATIONS

Hartmann et al., *Z. Chem.*, vol. 27, 1 (1987).
Kanazawa et al., *J. Poly. Sci. Pat A: Polymer Chemistry*, vol. 31, 1993, pp. 335–343.
Kanazawa et al., *J. Poly. Sci. Pat A: Polymer Chemistry*, vol. 31, 1993, pp. 1441–1447.
Kanazawa et al., *J. Poly. Sci. Pat A: Polymer Chemistry*, vol. 31, 1993, pp. 1467–1472.
Kanazawa et al., *J. Poly. Sci. Pat A: Polymer Chemistry*, vol. 31, 1993, pp. 2873–2876.
Messinger et al., *Arch. Pharm.*, 321 (1988), p. 89–92.
Panarin et al., *Makromol. Chem.*, Suppl. 9, p. 25–33, 1985.

* cited by examiner

*Primary Examiner*—Robert H. Harrison
(74) *Attorney, Agent, or Firm*—Keil & Weinkauf

(57) ABSTRACT

Use of polymers which contain
- (a) 0.1 to 100 mol % of vinylamine units or ethyleneimine units,
- (b) 0 to 99.9 mol % of units of at least one monomer from the group consisting of open-chain N-vinylcarboxamides, vinyl formate, vinyl acetate, vinyl propionate, vinyl alcohol, $C_1$- to $C_6$-alkyl vinyl ethers, monoethylenically unsaturated $C_3$- to $C_8$-carboxylic acids, their esters, nitriles, amides and anhydrides, N-vinylurea, N-vinylimidazoles and N-vinylimidazolines and
- (c) 0 to 5 mol % of units of monomers having at least two ethylenically unsaturated double bonds, in copolymerized form, the sum of (a), (b) and (c) in mol % always being 100, as biocide.

17 Claims, No Drawings

USE OF POLYMERS AS BIOCIDES

This is a 371 of application Ser. No. PCT/EP 97/01082, filed Mar. 4, 1997.

The invention relates to the use of polymers which contain
(a) 0.1 to 100 mol % of vinylamine or ethyleneimine units,
(b) 0 to 99.9 mol % of units of at least one monomer from the group consisting of N-vinylcarboxamides, vinyl formate, vinyl acetate, vinyl propionate, vinyl alcohol, $C_1$- to $C_6$-alkyl vinyl ethers, monoethylenically unsaturated $C_3$- to $C_8$-carboxylic acids, their esters, nitriles, amides and anhydrides, N-vinylurea, N-vinylimidazoles and N-vinylimidazolines and
(c) 0 to 5 mol % of units of monomers having at least two ethylenically unsaturated double bonds,
in copolymerized form as biocide.

Specifically functionalized polyvinyl alcohols, polyacrylates and polyethyleneimines for the immobilization of antimicrobially active substances are known from Z. Chem., Volume 27, 1 (1987). The active compounds are released in a controlled manner during the use of such systems. According to the information in the publication, the antimicrobial activity is based, however, on the release of the biocidal active compounds.

SU-A-1 071 630 discloses that copolymers of diallyldimethyl-ammonium chloride and sodium acrylate have a bactericidal activity. EP-A-0 331 528 discloses copolymers of ethylene and dialkylaminoalkylacrylamides having biocidal activity. Antimicrobially active polymers which contain vinylphosphonium and vinylsulfonium groups were reported in J. Polym. Sci. Part A: Polym. Chem., Volume 31, 335, 1441, 1467 and 2873 (1993) and also in Arch. Pharm. (Weinheim) 321, 89 (1988). Biocidally active copolymers of N-vinylpyrrolidone and vinylamines are known from Makromol. Chem., Suppl. Volume 9, 25 (1985).

It is an object of the present invention to make available novel biocidal agents.

We have found that this object is achieved according to the invention by the use of polymers which contain
(a) 0.1 to 100 mol % of vinylamine or ethyleneimine units,
(b) 0 to 99.9 mol % of units of at least one monomer from the group consisting of N-vinylcarboxamides of the formula

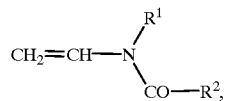

(I)

in which $R^1$, $R^2$=H or $C_1$- to $C_6$-alkyl,
vinyl formate, vinyl acetate, vinyl propionate, vinyl alcohol, $C_1$- to $C_6$-alkyl vinyl ethers, monoethylenically unsaturated $C_3$- to $C_8$-carboxylic acids, their esters, nitriles, amides and anhydrides, N-vinylurea, N-vinylimidazoles and N-vinylimidazolines and
(c) 0 to 5 mol % of units of monomers having at least two ethylenically unsaturated double bonds,
in copolymerized form, the sum of (a), (b) and (c) in mol % always being 100, as biocide.

The polymers described above are known from the prior art, cf. EP-B-0 071 050 and EP-B-0 216 387. The polymers comprising vinylamine units are obtainable, for example, by polymerizing mixtures which comprise (a) 0.1 to 100 mol % of open-chain N-vinylcarboxamides of the formula I indicated above,
(b) 0 to 99.9 mol % of at least one monomer from the group consisting of vinyl formate, vinyl acetate, vinyl propionate, $C_1$- to $C_6$-alkyl vinyl ethers, monoethylenically unsaturated $C_3$- to $C_8$-carboxylic acids, their esters, nitriles, amides and anhydrides, N-vinylimidazoles and N-vinylimidazolines and
(c) 0 to 5 mol % of at least one monomer having at least two ethylenically unsaturated double bonds,
and then partially or completely removing the group

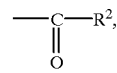

(II)

in which $R^2$ has the meaning indicated in formula I, from the copolymerized monomers of the formula I.

Open-chain N-vinylcarboxamides of the formula I are, for example, N-vinylformamide, N-vinyl-N-methylformamide, N-vinylacetamide, N-vinyl-N-methylacetamide, N-vinyl-N-ethylacetamide, N-vinyl-N-methylpropionamide and N-vinylpropionamide. The open-chain vinylcarboxamides can be employed in the polymerization on their own or as a mixture. Preferably, N-vinylformamide is used from this group of monomers.

The polymers comprising ethyleneimine units are polyethyleneimines which are obtainable by polymerization of ethyleneimine in the presence of acids, Lewis acids or acid-eliminating catalysts such as alkyl halides, e.g. methyl chloride, ethyl chloride, propyl chloride, methylene chloride, trichloromethane, carbon tetrachloride or tetrabromomethane. The polyethyleneimines, for example, have molecular weights Mw of 300 to 1,000,000. Polymers comprising ethyleneimine units of this type, which are obtainable by grafting polyamidoamines with ethyleneimine or by grafting polymers of open-chain N-vinylcarboxamides of the formula I with ethyleneimine, are additionally suitable. Grafted polyamidoamines are disclosed, for example, in U.S. Pat. No. 4,144,123.

As component (a), the polymers to be used according to the invention contain 0.1 to 100, preferably 10 to 90, mol % of vinylamine or ethyleneimine units. Of the polymers comprising ethyleneimine units, polyethyleneimine having molecular masses from 500 to 500,000 is preferably used.

Polymers comprising vinylamine units can be modified by copolymerizing monomers of the formula I with other monomers during the preparation. Suitable monomers include vinyl formate, vinyl acetate, vinyl propionate, $C_1$- to $C_6$-alkyl vinyl ethers, monoethylenically unsaturated $C_3$- to $C_8$-carboxylic acids, their esters, nitriles, amides and, if available, also the anhydrides, N-vinylurea, N-vinylimidazoles and N-vinylimidazolines. Examples of the mentioned monomers of group (b) are vinyl esters of saturated carboxylic acids having 1 to 6 carbon atoms, such as vinyl formate, vinyl acetate, vinyl propionate and vinyl butyrate, monoethylenically unsaturated $C_3$- to $C_8$-carboxylic acids, such as acrylic acid, methacrylic acid, dimethylacrylic acid, ethacrylic acid, crotonic acid, vinylacetic acid, allylacetic acid, maleic acid, fumaric acid, citraconic acid and itaconic acid as well as their esters, anhydrides, amides and nitriles. Preferably employed anhydrides are, for example, maleic anhydride, citraconic anhydride and itaconic anhydride.

Suitable esters which are derived, for example, from alcohols having 1 to 6 C atoms are methyl acrylate, methyl methacrylate, ethyl acrylate, ethyl methacrylate, isobutyl acrylate, hexyl acrylate or glycols or polyalkylene glycols, where in each case only one OH group of the glycols or polyglycols is esterified with a monoethylenically unsaturated carboxylic acid, e.g. hydroxyethyl acrylate, hydroxyethyl methacrylate, hydroxypropyl acrylate, hydroxypropyl methacrylate, hydroxybutyl acrylate and hydroxybutyl methacrylate. Acrylic acid monoesters and methacrylic acid monoesters of polyalkylene glycols of a molecular weight of up to 10,000, preferably 1500 to 9000, and esters of the mentioned carboxylic acids with aminoalcohols are, additionally suitable, e.g. dimethylaminoethyl acrylate, dimethylaminoethyl methacrylate, diethylaminoethyl acrylate, diethylaminoethyl methacrylate, dimethylaminopropyl acrylate and dimethylaminopropyl methacrylate. Suitable amides are, for example, acrylamide and methacrylamide. The basic acrylates can be employed in the form of the free bases, the salts with mineral acids or carboxylic acids or alternatively in quaternized form. Comonomers which are additionally suitable are acrylonitrile, methacrylonitrile, N-vinylimidazole and also substituted N-vinylimidazoles such as N-vinyl-2-methylimidazole and N-vinyl-2-ethylimidazole, N-vinylimidazoline and substituted N-vinylimidazolines, e.g. N-vinyl-2-methylimidazoline. Apart from the monomers mentioned, it is also possible to employ monomers comprising sulfo groups, such as, for example, vinylsulfonic acid, allylsulfonic acid, styrenesulfonic acid and 3-sulfopropyl acrylates as other monoethylenically unsaturated monomers.

The polymers comprising vinylamine units preferably contain
(a) 1 to 99 mol % of vinylamine units and
(b) 1 to 99 mol % of units of monomers from the group consisting of open-chain N-vinylcarboxamides, vinyl formate, vinyl acetate, vinyl propionate, $C_1$- to $C_6$-alkyl vinyl ethers, N-vinylurea, acrylic acid, methacrylic acid, maleic acid and also the anhydrides, esters, nitriles and amides of the carboxylic acids mentioned, N-vinylimidazoles, N-vinylimidazolines and/or vinyl alcohol units, the sum of (a), (b) and (c) in mol % always being 100.

The polymers comprising vinylamine units can additionally be modified to the effect that monomer mixtures are employed in the copolymerization which contain up to 5 mol % of a compound having at least two ethylenically unsaturated double bonds in the molecule as comonomer (c). Crosslinked copolymers then result which contain up to 5 mol % of units of monomers having at least two ethylenically unsaturated double bonds in the molecule in copolymerized form. If crosslinkers are employed in the copolymerization, the amount preferably used is 0.05 to 2 mol %. The additional use of the monomer (c) brings about a molecular weight increase of the copolymers. Suitable compounds of this type are, for example, methylenebisacrylamide, esters of acrylic acid or methacrylic acid with polyhydric alcohols, e.g. glycol dimethacrylate or glyceryl trimethacrylate as well as polyols which are esterified at least twice with acrylic acid or methacrylic acid, such as pentaerythritol and glucose. Suitable crosslinkers are additionally divinylethyleneurea, divinylbenzene, N,N'-divinylurea, divinyldioxane, pentaerythritol triallyl ether and pentaallylsucrose. Water-soluble monomers, for example glycol diacrylate or glycol diacrylates or glycol dimethacrylates of polyethylene glycols of a molecular weight of up to 3000, are preferably used from this group of compounds.

The copolymers have K values of 5 to 300, preferably 10 to 200, The K values are determined according to H. Fikentscher in 5% strength aqueous sodium chloride solution at pH 7, a temperature of 25° C. and a polymer concentration of 0.5% by weight.

The polymers comprising vinylamine units are prepared according to known processes by polymerizing open-chain N-vinylcarboxamides of the formula I with (b) 0 to 99.9 mol % of at least one monomer from the group consisting of vinyl formate, vinyl acetate, vinyl propionate, $C_1$- to $C_6$-alkyl vinyl ethers, monoethylenically unsaturated $C_3$- to $C_8$-carboxylic acids, their esters, nitriles, amides and anhydrides, N-vinylimidazoles and N-vinylimidazolines and (c) 0 to 5 mol % of at least one monomer having at least two ethylenically unsaturated double bonds in the presence or alternatively in the absence of inert solvents or diluents. The —CO—$R^2$ groups are then removed in a polymer-analogous reaction with formation of vinylamine units. Since polymerization in the absence of inert solvents or diluents usually leads to inhomogeneous polymers, polymerization in an inert solvent or diluent is preferred. Suitable inert diluents are, for example, those in which the open-chain N-vinylcarboxamides are soluble. Those suitable for solution polymerization are, for example, inert solvents such as methanol, ethanol, isopropanol, n-propanol, n-butanol, sec-butanol, tetrahydrofuran, dioxane, water and mixtures of the inert solvents mentioned. Polymerization can be carried out continuously or batchwise. It is carried out in the presence of free radical-forming polymerization initiators, which are employed, for example, in amounts from 0.1 to 20, preferably 0.05 to 10% by weight, based on the monomers. The polymerization can optionally be initiated solely by the action of energy-rich radiation, e.g. electron beams or UV rays.

In order to prepare polymers having a low K value, e.g. from 5 to 50, preferably 10 to 30, the polymerization is expediently carried out in the presence of regulators. Suitable regulators are, for example, organic compounds comprising sulfur in bound form. These include, for example, mercapto compounds, such as mercaptoethanol, mercaptopropanol, mercaptobutanol, mercaptoacetic acid, mercaptopropionic acid, butyl mercaptan and dodecyl mercaptan. Suitable regulators are additionally allyl compounds, such as allyl alcohol, aldehydes, such as formaldehyde, acetaldehyde, propionaldehyde, N-butyraldehyde and isobutyraldehyde, formic acid, ammonium formate, propionic acid, hydrazine sulfate and butenols. If the polymerization is carried out in the presence of regulators, 0.05 to 20% by weight thereof are needed, based on the monomers employed in the polymerization.

The polymerization of the monomers is customarily carried out in an inert gas atmosphere with exclusion of atmospheric oxygen. During the polymerization, provision is in general made for thorough mixing of the reaction participants. In the case of smaller batches in which safe dissipation of the heat of polymerization is guaranteed, the monomers can be copolymerized batchwise by heating the reaction mixture to the polymerization temperature and then allowing the reaction to proceed. In this case, these temperatures are in the range from 40 to 180° C., it being possible to work at normal pressure, reduced pressure or alternatively elevated pressure. Polymers having a high molecular weight are obtained if the polymerization is carried out in water. This can be carried out, for example, for the preparation of water-soluble polymers in aqueous solution, as a water-in-oil emulsion or according to the reverse suspension polymerization process.

In order to avoid hydrolysis of the monomeric N-vinylcarboxamides during the polymerization in aqueous solution, the polymerization is preferably carried out in a pH range from 4 to 9, in particular from 5 to 8. In many cases, it is recommended to additionally work in the presence of buffers, e.g. to add primary or secondary sodium phosphate to the aqueous phase.

By removal of groups of the formula

from the monomer units of the formula III with formation of amine or ammonium groups, the polymers comprising vinylamine units to be used according to the invention:

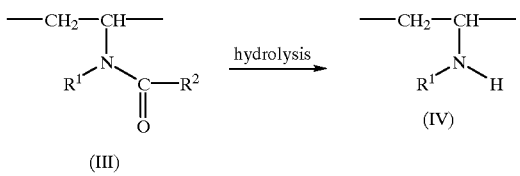

are obtained from the polymers described above.

The substituents $R^1$ and $R^2$ in the formulae (II) to (IV) in each case have the meaning indicated in formula I.

The hydrolysis is preferably carried out in the presence of water under the action of acids, bases or enzymes, but can also take place in the absence of acids, bases or enzymes. Depending on the reaction conditions during the hydrolysis, i.e. the amount of acid or base, based on the polymer to be hydrolyzed, and the reaction temperature during the hydrolysis, various degrees of hydrolysis are obtained. The hydrolysis is carried out until 0.1 to 100 mol %, preferably 1 to 99 mol %, of the copolymerized monomer units III are removed from the polymer. According to the invention, those polymers are particularly preferably employed which contain 1 to 99 mol % of vinylamine units and 1 to 99 mol % of units of the formula III, preferably N-vinylformamide units, the sum of the data in mol % always being 100.

Acids suitable for the hydrolysis are, for example, mineral acids, such as hydrogen halide (gaseous or in aqueous solution), sulfuric acid, nitric acid, phosphoric acid (ortho-, meta- or polyphosphoric acid) and organic acids, e.g. $C_1$- to $C_5$-carboxylic acids, such as formic acid, acetic acid and propionic acid, or the aliphatic or aromatic sulfonic acids, such as methanesulfonic acid, benzenesulfonic acid or toluenesulfonic acid. Hydrochloric acid or sulfuric acid is preferably used for the hydrolysis. During hydrolysis with acids the pH is 0 to 5. 0.05 to 1.5 equivalents of acid, preferably 0.4 to 1.2, for example, are needed per formyl group equivalent in the polymer.

During hydrolysis with bases, metal hydroxides of metals of the first and second main group of the Periodic Table can be used, for example lithium hydroxide, sodium hydroxide, potassium hydroxide, calcium hydroxide, strontium hydroxide and barium hydroxide are suitable. Likewise, however, it is also possible to use ammonia and alkyl derivatives of ammonia, e.g. alkyl- or arylamines, e.g. triethylamine, monoethanolamine, diethanolamine, triethanolamine, morpholine or aniline. During hydrolysis with bases the pH is 8 to 14. The bases can be employed in solid, liquid or, if appropriate, alternatively in the gaseous state in diluted or undiluted form. Bases preferably used for the hydrolysis are ammonia, sodium hydroxide solution or potassium hydroxide solution. Hydrolysis in the acidic or in the alkaline pH range is carried out, for example, at temperatures from 30 to 170, preferably 50 to 120° C. It is complete after approximately 2 to 8, preferably 3 to 5, hours. A procedure has proven particularly suitable in which, for hydrolysis, the bases or acids are added in aqueous solution. After hydrolysis, inter alia, a neutralization is carried out such that the pH of the hydrolyzed polymer solution is 2 to 8, preferably 3 to 7. The neutralization is necessary if a progression of the hydrolysis of partially hydrolyzed polymers is to be avoided or delayed. The hydrolysis can also be carried out with the aid of enzymes.

During the hydrolysis of copolymers of open-chain N-vinylcarboxamides of the formula I and at least one of the abovementioned suitable comonomers, optionally a further modification of the polymers occurs in which the copolymerized monomers are also hydrolyzed. Thus vinyl alcohol units result, for example, from copolymerized units of vinyl esters. Depending on the hydrolysis conditions, the copolymerized vinyl esters can be completely or partially hydrolyzed. In the case of partial hydrolysis of copolymers comprising vinyl acetate units in copolymerized form, the hydrolyzed copolymer gains, in addition to unchanged vinyl acetate units, vinyl alcohol units and units of the formulae III and IV. Carboxylic acid units result from units of monoethylenically unsaturated carboxylic anhydrides during the hydrolysis. Copolymerized monoethylenically unsaturated carboxylic acids are chemically unchanged during the hydrolysis. However, ester and amide units hydrolyze to carboxylic acid units. Units of amides or carboxylic acids, for example, result from copolymerized monoethylenically unsaturated nitriles. Vinylamine units can likewise be formed from copolymerized N-vinylurea. The degree of hydrolysis of the copolymerized comonomers can easily be determined analytically.

Polymers are preferably used which contain
(a) vinylamine units and
(b) N-vinylformamide, vinyl formate, vinyl acetate, vinyl propionate, vinyl alcohol and/or N-vinylurea units
in copolymerized form. Polymers which are preferably to be employed contain
(a) 0.1 to 100 mol % of vinylamine units or ethyleneimine units and
(b) 0 to 99.9 mol % of N-vinylformamide units.

These polymers are either partially or completely hydrolyzed homopolymers of vinylformamide or are polyethyleneimines.

The partially hydrolyzed homopolymers of N-vinylformamide preferably contain
(a) 1 to 99 mol % of vinylamine units and
(b) 1 to 99 mol % of N-vinylformamide units
in copolymerized form and have a K value of 5 to 300 (determined according to H. Fikentscher in 0.1% strength by weight aqueous sodium chloride solution at 25° C. and a polymer concentration of 0.5% by weight). Particularly preferably, those hydrolyzed homopolymers of N-vinylformamide are employed which contain
(a) 10 to 90 mol % of vinylamine units and
(b) 10 to 90 mol % of N-vinylformamide units in copolymerized form and have a K value of 10 to 120 (determined according to H. Fikentscher in 0.1% strength sodium chloride solution at 25° C. and a polymer concentration of 0.5% by weight). The sum of (a) and (b) in mol % is always 100.

The polymers described above have a very good action against microorganisms. They have microbicidal and microbistatic properties. They are therefore suitable as biocidal active compounds in the production of disinfectants and as active compounds for the preservation of industrial products such as dispersions, emulsions, colorants, coatings, drilling and cutting oils and also detergents and cleansers. They can also be employed as biocidal active compounds in paper manufacture, e.g. for slime control. They are furthermore suitable for the biocidal finishing of industrial products such as paints, fabrics, nonwovens and carpet coatings and can additionally be used for the protection of, for example, cooling water circulations and other industrial waterconducting systems against microbial contamination. The polymers to be used according to the invention can be used in all detergents and cleansers. Suitable compositions for detergents and cleansers are indicated, for example, in R.D. No. 377 26 (1995).

The K values of the polymers were determined according to H. Fikentscher, Cellulose-Chemie [Cellulose Shemistry], Volume 13, 58 to 64 and 71 to 74 (1932) in 5% strength by weight aqueous sodium chloride solution at 25° C. and pH 7 and a polymer concentration of 0.5% by weight.

Microbicidal and microbistatic properties are determined experimentally. Very highly suitable test methods for the testing of disinfectants have been described in detail by the Deutschen Gesellschaft für Hygiene und Mikrobiologie [German Association for Hygiene and Microbiology, DGHM].

Tube dilution tests were carried out according to the "Guidelines for the testing and assessment of chemical disinfection procedures (Status 01.01.81, procedure slightly modified)" using caseine peptone-soybean flour peptone medium. Dilution was carried out using water of standardized hardness without further auxiliaries such as, for example, surfactants. The adjustment of the pH to 7.2±0.2 was carried out using 0.1 mol/l NaOH or 0.1 mol/l HCl. The grading of the test concentrations was carried out according to the concentration stages proposed by the DGHM. Assessment was carried out after incubation at 36° C. for 72 hours.

Table 1 which follows indicates the strain numbers of the microorganisms and the "minimum effective concentration" ("MIC value"). The concentrations are based on the respective content of polymer having 97 mol % of vinylamine units and 3 mol % of vinylformamide units. The K value of the polymer was 31.

TABLE 1

| Test microorganism | | MIC value |
|---|---|---|
| Staphylococcus aureus | ATTC 6538 | 1400 ppm |
| Escherichia coli | ATTC 11229 | 700 ppm |
| Proteus mirabilis | ATTC 14153 | 2100 ppm |
| Pseudomonas aeruginosa | ATTC 15442 | 350 ppm |
| Candida albicans | ATTC 10231 | 700 ppm |

The biocidal action was also determined by measurements in a Malthus apparatus (Malthus Flexi M 2060, Malthus Instruments Limited). 3 ml of TSB medium (tryptone soya broth) were added to the outer chamber of a Malthus apparatus. 0.5 ml of sterile KOH (0.1M) was filled into the inner chamber. The polymers to be tested were added to the TSB medium. Concentration series were tested in each case. The media were inoculated with $10^3$ colony-forming units per ml [CFU/ml] in each case. Incubation was then carried out in the Malthus incubator. Growing cells produce $CO_2$, which dissolves in the KOH of the inner chamber and thereby alters the conductivity of the KOH. The alteration of the conductivity is measured by the Malthus apparatus. The detection time for the start of growth was recorded and evaluated.

Microbistatic activity was detectable when, after inoculation, the start of growth was delayed or failed to occur. The minimum effective concentration (MIC value) was the lowest polymer concentration in each case which prevented growth over a period of 100 h (cf. the results in Tables 2 and 3).

In Table 2, MIC values of polyvinylamine with a K value of 30 are indicated for gram-positive and gram-negative test microorganisms.

TABLE 2

| | MIC value for polyvinylamine [ppm] |
|---|---|
| Grain-positive test microorganisms: | |
| Bacillus subtilis | 500 |
| Listeria monocytogenes | 1000 |
| Staphylococcus aureus | 500 |
| Streptococcus mutans | 500 |
| Gram-negative test microorganisms: | |
| Escherichia coli | 4000 |
| Pseudomonas aeruginosa | 4000 |
| Pseudomonas fluorescens | 2000 |
| Shewanella putrefaciens | 1000 |
| Vibrio parahaemolyticus | 1000 |

In Table 3, MIC values are indicated for various polymers.

TABLE 3

| | MIC value [ppm] for | | | |
|---|---|---|---|---|
| | Bacillus subtilis | Staphylococcus aureus | Pseudomonas fluorescens | Shewanella putrefaciens |
| a) Copolymer, comprising 70 mol % of vinylamine units and 30 mol % of vinyl alcohol units, K value 49 | 100 | 100 | | |
| b) Copolymer, comprising 80 mol % of vinylamine units and 20 mol % of N-vinylurea units, K value 80 | 100 | 500 | 2000 | 2000 |

For determination of the microbicidal action, dilution series in a factor of 10 stages were set up for all test organisms of cell suspensions having $10^8$ CFU/ml. For each dilution stage, the respective detection time for the start of growth was measured. Calibration curves could be derived from this which show CFU/ml inoculation density as a function of the detection time.

The polymers to be tested were added to cell suspensions of $10^4$ CFU/ml. After 30 min, the outer chambers in the Malthus apparatus were inoculated with 0.1 ml of this polymer-treated cell suspension in each case. The detection time for the start of growth was measured. If growth did not occur, an aliquot was plated out on agar for checking.

With the aid of the calibration curve, the number of colony-forming units which had survived the polymer treatment could be back-calculated from the measured detection time. Division by the starting microorganism count ($10^4$ CFU/ml) afforded the destruction factor.

The indirect back-calculation of the CFU after polymer treatment avoided the CFU having to be determined directly from polymer-treated suspensions. Direct determination could have led to misinterpretations as a result of flocculation and agglomeration of the bacteria.

The microbicidal activity was determined for cells of the stationary growth phase from the destruction factor. The minimum effective microbicidal concentration (MBC) was the concentration which reduced the number of CFU by 99% within 30 min. The results are indicated in Table 4.

TABLE 4

| | MBC values | | | |
|---|---|---|---|---|
| | Streptococcus mutans | Staphylococcus aureus | Pseudommes fluorescens | Shewanella putrefaciens |
| Polyvinylamine, K value 30 | 500 | 100 | >2000 | >2000 |
| Copolymer, comprising 70 mol % of vinylamine units and 30 mol % of vinyl alcohol units, K value 49 | 2000 | 100 | 500 | 500 |
| Copolymer, comprising 80 mol % of vinylamine units and 20 mol % of N-vinylurea units, K value 80 | 500 | 100 | 2000 | 2000 |

What is claimed is:

1. A method for preventing the growth of microorganisms, which method comprises treating the microorganisms with a microbicidal or microbistatic effective amount of a polymer which comprises, in copolymerized form
   (a) vinylamine units or ethyleneimine units;
   (b) units of at least one monomer selected from the group consisting of an N-vinylcarboxamide of formula

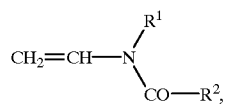
(I)

wherein $R^1$ and $R^2$ is hydrogen or $C_1$–$C_6$-alkyl; vinyl formate; vinyl acetate; vinyl propionate; vinyl alcohol; a $C_1$–$C_6$-alkyl vinyl ether; a monoethylenically unsaturated $C_3$–$C_8$-carboxylic acid or an ester, nitrile, amide or anhydride thereof; N-vinylurea; an N-vinylimidazole and an N-vinylimidazole; and
   (c) 0 to 5 mol % of units of monomers having at least two ethylenically unsaturated double bonds; wherein
      i) component (a) is present in an amount of from 10 to 90 mol % or,
      ii) in the event that component (a) are vinylamine units, each of components (a) and (b) is present in an amount of from 1 to 90 mol %,
   the sum of (a), (b) and (c) in mol % in each case being 100.

2. The method of claim 1 wherein, component (b) contains units of at least one member selected from the group consisting of N-vinylformamide, vinyl formate; vinyl acetate; vinyl propionate; vinyl alcohol and N-vinylurea.

3. The method of claim 1 wherein N-vinylformamide units are present as component (b).

4. The method of claim 1 wherein 10 to 90 mol % of vinylamine units are present as component (a) and 10 to 90 mol % of N-vinylformamide units are present as component (b).

5. The method of claim 1 wherein the polymer has a K value in the range of from 5 to 300.

6. The method of claim 1 wherein the microorganism is a bacteria or a yeast, or a mixture thereof.

7. The method of claim 6 wherein the microorganism is a bacteria.

8. The method of claim 7 wherein the bacteria is selected from the group consisting of gram-negative and gram-positive bacteria, or a mixture thereof.

9. The method of claim 1, wherein the polymer comprises, in copolymerized form
   (a) from 1 to 99 mol % of vinylamine units;
   (b) from 1 to 99 mol % of units of at least one monomer selected from the group consisting of an N-vinylcarboxamide of formula

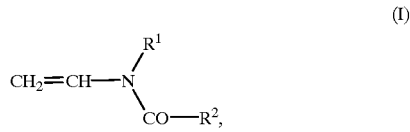
(I)

wherein $R^1$ and $R^2$ is hydrogen or $C_1$–$C_6$-alkyl; vinyl formate; vinyl acetate; vinyl propionate; vinyl alcohol; a $C_1$–$C_6$-alkyl vinyl ether; a monoethylenically unsaturated $C_3$–$C_8$-carboxylic acid or an ester, nitrile, amide or anhydride thereof; N-vinylurea; an N-vinylimidazole and an N-vinylimidazole; and
   (c) from 0 to 5 mol % of units of monomers having at least two ethylenically unsaturated double bonds.

10. The method of claim 1, wherein the polymer comprises, in copolymerized form
   (a) from 10 to 90 mol % of vinylamine units or ethyleneimine units;
   (b) from 10 to 90 mol % of units of at least one monomer selected from the group consisting of an N-vinylcarboxamide of formula

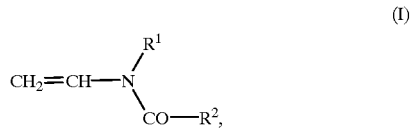
(I)

wherein $R^1$ and $R^2$ is hydrogen or $C_1$–$C_6$-alkyl; vinyl formate; vinyl acetate; vinyl propionate; vinyl alcohol; a $C_1$–$C_6$-alkyl vinyl ether; a monoethylenically unsaturated $C_3$–$C_8$-carboxylic acid or an ester, nitrile, amide or anhydride thereof; N-vinylurea; an N-vinylimidazole and an N-vinylimidazole; and
   (c) 0 to 5 mol % of units of monomers having at least two ethylenically unsaturated double bonds.

11. The method of claim 10 wherein vinylamine units are present as component (a), and component (b) contains units of at least one member selected from the group consisting of N-vinylformamide, vinyl formate; vinyl acetate; vinyl propionate; vinyl alcohol and N-vinylurea.

12. The method of claim 10 wherein N-vinylformamide units are present as component (b).

13. The method of claim 10 wherein 10 to 90 mol % of vinylamine units are present as component (a) and 10 to 90 mol % of N-vinylformamide units are present as component (b).

14. The method of claim 10 wherein the polymer has a K value in the range of from 5 to 300.

15. The method of claim 10 wherein the microorganism is a bacteria or a yeast, or a mixture thereof.

16. The method of claim 15 wherein the microorganism is a bacteria.

17. The method of claim 16 wherein the bacteria is selected from the group consisting of gram-negative and gram-positive bacteria, or a mixture thereof.

* * * * *

UNITED STATES PATENT AND TRADEMARK OFFICE
CERTIFICATE OF CORRECTION

PATENT NO.    : 6,261,581 B1
DATED         : July 17, 2001
INVENTOR(S)   : Gebhardt et al.

It is certified that error appears in the above-identified patent and that said Letters Patent is hereby corrected as shown below:

<u>Column 9, claim 1,</u>
Line 48, "90" should be -- 99 --.

<u>Column 9, claim 2,</u>
Line 50, after "wherein" insert -- vinylamine units are present as component (a), and --.

Signed and Sealed this

Second Day of April, 2002

Attest:

JAMES E. ROGAN
*Attesting Officer*        *Director of the United States Patent and Trademark Office*